United States Patent [19]

Kruse et al.

[11] Patent Number: 4,645,839
[45] Date of Patent: Feb. 24, 1987

[54] SULPHUR DEHYDROGENATION PROCESS TO YIELD 5-METHYL-2-PYRIDONE

[75] Inventors: Walter M. Kruse, Wilmington, Del.; John F. Stephen, West Chester, Pa.

[73] Assignee: ICI Americas Inc., Wilmington, Del.

[21] Appl. No.: 725,680

[22] Filed: Apr. 22, 1985

Related U.S. Application Data

[63] Continuation of Ser. No. 450,780, Dec. 17, 1982, abandoned.

[51] Int. Cl.[4] ........................................... C07D 211/86
[52] U.S. Cl. .................................................... 546/290
[58] Field of Search ......................................... 546/290

[56] References Cited

PUBLICATIONS

Fieser & Fieser, Reagents for Organic Synthesis, vol. I, p. 713, Wiley Publishers, 1967.
Fieser & Fieser, Reagents for Organic Synthesis, vol. 6, pp. 556–557, Wiley-Interscience Publishers, (1977).
Shono et al, "A New Practical Synthesis of 5-Hydroxy-3,4-dihydrocarboxtyril and 5-Hydroxycarbostyril", *J. Org. Chem.*, vol. 46, p. 3719 (1981).
Herz et al, "Pyrrolopyridines.IV.Synthesis of Possible Intermediates", *J. Org. Chem.*, vol. 26, pp. 122–125 (1961).
Davies et al, "Intramolecular Cycloaddition Reactions of Mono- and Di-hydroxypryimidines", *J.C.S. Perkin I*, pp. 1293–1297 (1978).
Al-Hajjar et al, "Reactions of $\alpha,\beta$-Unsaturated Ketones with Cyanoacetamide", *J. Heterocyclic Chem.*, vol. 17, pp. 1521–1525 (1980).
Seoane, et al, "Synthesis of Heterocyclic Compounds XIX[1] Preparation of 4,6-Diaryl-3,5-Dicyano-2-Pyridones", *Heterocycles*, vol. 14, pp. 639–642, No. 5, (1980).
Shamma et al, "Unsaturated Lactams. II.[1] The Catalytic Dehydrogenation of $\alpha,\beta$-Unsaturated Valero-Lactams to Pyridones[2]", vol. 26, pp. 2586–2587 (1961).
Trolliet et al, "Obtention de Pyrones-2, Par Deshydrogenation de Lactones d'Enol", *Bulletin de la Societe Chimique de France*, No. 7–8, pp. 1484–1486, (1974).
Spath et al, "Uber Peganin-Derivate und ihre Pikrolonate", *Berichte der Deutschen Chemischen Gesellschaft*, vol. 69, pp. 2052–2061 (1936).
Muller et al, "Methoden der Organischen Chemie", *Georg Thieme Verlag Stuttgart*, pp. 391–418 (1981).

*Primary Examiner*—Alan L. Rotman
*Attorney, Agent, or Firm*—John Wilson Jones; John M. Sheehan

[57] ABSTRACT

A method for synthesizing the aromatic compound 5-methyl-2-pyridone from the corresponding 3,4-dihydro compound by dehydrogenation using sulphur. Particular advantages are achieved by reaction at about 180° C. or less. The product is useful as an intermediate for the preparation of various pyridyloxyphenoxy herbicides.

10 Claims, No Drawings

SULPHUR DEHYDROGENATION PROCESS TO YIELD 5-METHYL-2-PYRIDONE

This is a continuation of co-pending application Ser. No. 450,780 filed on Dec. 17, 1982, now abandoned.

BACKGROUND OF THE INVENTION

Various 4-(5-halomethyl-2-pyridyloxy)phenoxy compounds are known to be useful as herbicides as disclosed in European Published Patent Application No. 483, United Kingdom Patent Specification Nos. 1,599,121 and 1,599,126 and U.S. Pat. Nos. 4,184,041 and 4,317,913. For example, butyl 2-[4-(5-trifluoromethyl-2-pyridyloxy)phenoxy]propionate which is also known as fluazifopbutyl is an effective grass herbicide which can be used in fields where broad-leaved crops such as cotton and soybeans are cultivated. Important starting materials for such pyridyloxyphenoxy compounds are the 2-halo-5-trichloromethylpyridines such as 2-chloro-5-trichloromethylpyridine described in U.S Pat. No. 4,317,913. Such 2-halo-5-trichloromethylpyridines, in turn, may be prepared by chlorinating, under ultraviolet light irradiation, a 2-halo-5-methylpyridine as described in U.S. Pat. No. 4,152,328. One starting material for 2-halo-5-methylpyridine is the corresponding hydroxy compound 2-hydroxy-5-methylpyridine, also known as 5-methyl-2-pyridone, of the following formula (I):

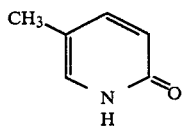
(I)

as disclosed by W. Herz et al. in the Journal of Organic Chemistry, Vol. 26 pages 122–125 (1961).

In the proposed synthetic schemes for the pyridyloxyphenoxy herbicides one object has been the synthesis of 2-halo-5-methylpyridines without utilizing pyridine, and in particular 3-picoline, picoline, starting materials to thus avoid the problems of by-product formation in the halogenation reaction to yield 2-halo-5-methylpyridine. This object was achieved in copending U.S. Ser. No. 433,273 filed Oct. 7, 1982, now U.S. Pat. No. 4,473,696, assigned to the assignee of the present invention. In U.S. Pat. No. 4,473,696, the pyridone of formula (I) was synthesized from propionaldehyde and an acrylic compound of the formula $CH_2=CH-Y$, where $Y=COOR$, $-CONH_2$ or CN and R is an organic moiety such as alkyl, through 5-methyl-3,4-dihydro-2(1H)-pyridone of the following formula (II):

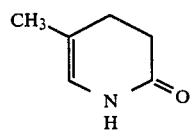
(II)

The dihydropyridone of formula (II) was disclosed as being dehydrogenated, or oxidized, to (I) by a two-step process comprising the halogenation of (II) across the double bond followed by dehydrohalogenation with loss of two moles of hydrogen halide to thus produce two double bonds which results in the structure (I).

Dehydrogenation of various dihydro hydrocarbon and hetroatomic rings is known to proceed with sodium nitrite and sulfuric acid, palladium on carbon, sulphur and selenium, usually at very high temperatures, e.g., over 200° C. Literature citations include C. Seoane et al. in Heterocycles, Vol. 14, No. 5, pages 639–642 (1980); F. Al-Hajjar et al. in the Journal of Heterocyclic Chemistry, Vol. 17, pages 1521–1525 (1980): M. Trolliet et al. in the Bulletin de la Societe Chimique De France, No. 7-8, pages 1484–1486 (1974); T. Shono et al. in the Journal of Organic Chemistry, Vol. 46 page 3719 (1981): M. Shamma et al. in the Journal of Organic Chemistry, Vol. 26, pages 2586–2587 (1961); L. Davies et al. in the Journal of the Chemical Society, Perkins Transactions I, pages 1293–1297 (1978): E. Spaeth et al. in Berichte der Deutschen Chemischen Gesellschaft Vol. 69, pages 2060–2061 (1936): in "Methoden der Organischen Chemie" (Houben Weyl) Band IV/A, Georg Thieme Verlag, Stuttgart, pages 391–418 (1981) and particularly pages 405–416: and in "Reagents for Organic Synthesis" by L. F. Fieser at pages 1118–1120, John Wiley and Sons Inc. (1967). However, disadvantages of prior processes include the problem of containing the highly poisonous $H_2Se$ when using Se° as the dehydrogenation agent, the use of high temperatures which increases production costs and which may cause excessive by-product formation, the use of catalysts which cause disproportionation, e.g., the production of both aromatic and saturated species from an unsaturated starting material, and the incorporation of one or more atoms of the reagent used into the molecule to be dehydrogenated, e.g., exchange of oxygen in the starting material with sulphur in the dehydrogenation agent.

It is an object of the present invention to provide a one step, low temperature, relatively mild reaction to synthesize (I) from (II) in high yield and with an inexpensive and safe reagent as well as under safe reaction conditions.

SUMMARY OF THE INVENTION

5-Methyl-2-pyridone is synthesized from 5-methyl-3,4-dihydro-2(1H)pyridone by reaction with sulphur, preferably at a moderate temperature of about 180° C. or less, e.g., about 130° to 160° C. The reaction proceeds smoothly with minimal by-product formation and allows a rapid and simple recovery of product to the extent that the reaction product mixture may simply be taken on to a subsequent step, e.g., a chlorination, without purification of the product.

DETAILED DESCRIPTION OF THE INVENTION

The synthesis of 5-methyl-2-pyridone of formula (I):

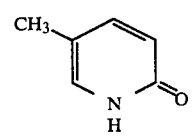
(I)

is accomplished according to the invention by the dehydrogenation of 5-methyl-3,4-dihydro-2(1H)pyridone of formula (II):

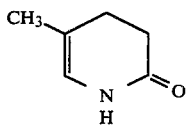

(II)

in the presence of sulphur. Preferably, the reaction is conducted in a single step.

The reaction temperature for the dehydrogenation is preferably about 180° C. or less, e.g., about 150° C. or less. Above this temperature, oxygen in the starting material may begin to exchange with the elemental sulphur to produce the corresponding thiocompound. However, at 180° C. or below, it was surprisingly found that the desired reaction did take place at a reasonable rate and without excessive by-product formation. A suitable temperature range is about 130° to 160° C., with the most preferred range being about 130° to 140° C. Reaction between about 150° C. and 180° C. produced a discolored product with, surprisingly, maintenance of reasonable yields.

The surprising result of reaction at the moderate temperatures described may be due to assistance of the breakage of —S—S— bonding in the elemental sulphur by the starting material itself, e.g., by the nitrogen atom in the starting material or the product of the reaction. Thus, the reaction need only be conducted with the starting material, sulphur and a solvent to allow the reaction product mixture to be taken on to a further step without the complications inherent in the use of a catalyst, e.g., the problem of catalyst removal.

The molar ratio of sulphur:the dihydropyridone of formula (II) is preferably less than about 2:1 since above this ratio, sulphur will tend to co-crystallize in the reaction product. Rapid formation of crystals of the reaction product is an advantage of the present invention since the pyridone (I) is obtained in high purity with simple filtration, as opposed to first recovering a catalyst such as palladium by filtration followed by a second filtration or other recovery step or steps. A suitable range of sulphur:dihydropyridone (II) is just over about 1:1 to less than 2:1, e.g., slightly more than 1:1 to about 1.3:1, with the most preferred ratio being about 1:1.

The dehydrogenation reaction of the invention may be conducted neat or in the presence of a solvent, in particular, one which is unreactive towards the starting material and product at the temperature used for reaction. It is preferred to use a solvent in the reaction since the melting point of the product is about 178° C. and if product solidifies during the reaction itself, it will enclose starting material in the crystalline formation. Preferably, the solvent has a boiling point of at least about 135° C. It is preferred to use a solvent which does not contain oxygen so as to avoid possible oxygen-sulphur exchange. Aromatic solvents have been found to be useful, in particular aromatic hydrocarbons such as alkylated aromatic hydrocarbons, e.g., alkylbenzenes such as Tenneco 500-100 available from Tenneco Oil Company of Houston, Tex. or mesitylene, and aromatic halogenated hydrocarbons such as monochlorobenzene, dichlorobenzene, e.g., ortho-dichlorobenzene, trichlororbenzene, e.g., 1,2,3-, 1,2,4- or 1,3,5-trichlorobenzene.

Hydrogen sulfide produced during the dehydrogenation reaction is advantageously removed continuously. Removal may be by simply maintaining a slight vacuum on the reaction mixture or by passing at inert gas, e.g., nitrogen, through the mixture. The hydrogen sulfide may be discarded, e.g., by dissolving in a basic solution such as an aqueous sodium hydroxide solution or may be recycled to elemental sulphur by the Claus process as described in the "Encyclopedia of Chemical Technology" (Kirk-Othmer), John Wiley & Sons, Inc., New York at pages 352–354 (1969). During the course of the reaction, the presence of oxygen should be avoided since it appears that the oxidation becomes uncontrolled.

Recovery of the compound of formula (I) may be accomplished by decreasing the reaction temperature, e.g., by cooling to room temperature, and allowing the product to crystallize out of the solvent. An advantage of the present invention is that the product of formula (I) does spontaneously crystallize from the reaction mixture in both high yield and in a pure form. Filtration of the thus-cooled reaction medium yields crystals of the desired product. In order to increase effective yields of the desired product and to eliminate purification or recovery steps, the reaction product may simply be extracted with water whereby the product goes into the aqueous solution and the unreacted sulphur is eliminated.

In the following Examples and throughout the specification, the following abbreviations are used: °C. (degrees Centigrade): ml (milliliters): g (grams): m (moles); mmoles (millimoles): mm (millimeters); GLC (gas liquid chromatography); GC/MS (gas chromatograph-mass spectrometry): IR (infrared): NMR (nuclear magnetic resonance): mp (melting point): bp (boiling point): $d_6$-DMSO (deuterated dimethyl sulfoxide); MCB (monochlorobenzene); DHP (5-methyl-3,4-dihydro-2(1H)pyridone); HMP (2-hydroxy-5-methylpyridine): HPLC (high pressure liquid chromatography): TCB (1,2,4-trichlorobenzene); and the conventional symbols for the chemical elements.

REFERENCE EXAMPLE 1

A 500 ml 4-neck flask was equipped with a stirrer, thermometer, addition funnel and condenser. To the flask was charged 191.7 g (2.2 m) of morpholine and 138.2 g (1 m) of potassium carbonate (anhydrous) and the mixture was stirred and cooled to −5° C. with an ice-salt bath. To the flask was added 58 g (1 m) of propionaldehyde over a period of 55 minutes at a pot temperature of −5° C. The temperature was then allowed to rise to 25° to 27° C. and the reaction was continued for 2 hours at 25° C. The product was filtered and the filter cake washed with four 15 ml washes of toluene. The fitrate was heated under vacuum while morpholine was stripped using a 1 foot Vigreux column. This treatment was carried out at an oil bath temperature of 85° to 112° C., a pot temperature of 70° to 90° C., a vapor temperature of 41° to 58° C. and at a pressure of approximately 35 to 40 mm of Hg. The vacuum stripping was carried out until 133.3 g of product was obtained as a residue GLC and GC/MS established that the predominant product was 4-(2-propenyl)morpholine. $^{13}C$ NMR in $d_6$-DMSO (in δ units):15.2 (CH$_3$); 95.1 (CH$_3$—CH)=; 140.8 (—CH=CH—); 49.4 (—N(—CH$_2$—)$_2$); and 66.1 (O(—CH$_2$—)$_2$).

REFERENCE EXAMPLE 2

A solution of 40 g of crude morpholinopropene produced in Reference Example 1 in 175 ml of acetonitrile is cooled to −2° C. in an ice-salt bath and treated with a solution of 30.5 g (0.35 m) of methylacrylate in 70 ml of acetonitrile dropwise over a period of 20 minutes at −2° to 0° C. The temperature of the solution is then gradually raised and held at 66° to 76° C. for 17 hours. At that point, a predominate product peak can be detected by GLC together with a smaller unidentified peak while at the same time, the morpholinopropene peak has almost completely disappeared. The methyl 3-methyl-2-(4-morpholinyl)cyclobutane carboxylate was characterized by GC/MS and NMR.

$^{13}$C NMR in d$_6$-DMSO (in δ units):66.3 (O(—CH$_2$—)$_2$); 50.2 (—N(—CH$_2$—)$_2$); 70.8 (N—CH); 31.0 (CH$_3$—CH); 26.2 (cyclobutane—CH$_2$—); 39.1 (CH—COOCH$_3$); 174.1 (—COOCH$_3$); 51.4 (—COOCH$_3$); and 20.6 (CH—CH$_3$).

REFERENCE EXAMPLE 3

A solution of 18 g (0.3 m) of acetic acid in 120 ml of water is added to the crude morpholino cyclobutane carboxylate ester product of Reference Example 2 and the reaction mixture is heated at 70° to 79° C. for 5 hours. The product solution is cooled to room temperature, diluted with 150 ml of water and extracted 3 times with ethyl acetate, 100 ml each wash. The extracts were washed 2 times with dilute sodium chloride brine solution and methyl 4-formylpentanoate is obtained after vacuum stripping at 60° to 70° C. and a moderate vacuum of 100 mm to 28 mm of Hg in a yield of 29.2 g.

The crude methyl 4-formylpentanoate obtained above was purified by distillation at 83° to 85° C. at 6 mm to 8 mm of Hg with 90% recovery. Purity by GLC after distillation was determined to be 95.3% and the product was characterized by IR, NMR and GC/MS.

$^{13}$C NMR in d$_6$-DMSO (in δ units):51.4 (—COOCH$_3$); 173.2 (—COOCH$_3$); 31.0 (—CH$_2$—COOCH$_3$); 25.4 (—CH$_2$—CH$_2$—COOCH$_3$); 45.1 (CH—CH$_3$); 13.0 (CH—CH$_3$); and 204.7 (—CHO).

REFERENCE EXAMPLE 4

To 1.44 g (0.01 m) of methyl 4-formylpentanoate dissolved in 10 ml of acetic acid was added 1.54 g (0.02 m) of ammonium acetate and the mixture was heated at 80° to 125° C. for 16 hours. GLC showed about 11% unreacted starting material, 89% of the desired title product and no by-products. The product was vacuum stripped, dissolved in 10 ml of ethyl acetate and washed 4 times with water, 2.5 ml each wash. The product was distilled after vacuum stripping of ethyl acetate to yield 0.5 g of 5-methyl-3,4-dihydro-2(1H)pyridone, bp 103° C. at 0.5 mm of Hg. The product was recrystallized from ethyl acetate, mp, 76° to 78° C.

Elemental Analysis: N, 12.13% (Calculated 12.8%). $^{13}$C NMR in d$_6$-DMSO (in δ units):19.0 (CH$_3$); 169.0 (C=O); 30.1 (CH$_2$ α to C=O); 25.5 (CH$_2$ β to C=O); 112.0 (C(CH$_3$)=CH); and 120.3 (CH directly attached to NH)

EXAMPLE 1

DHP of 86% purity (as determined by GLC) (1.33 g, 12 mmole), sulfur (0.416 g, 13 mmole) and 3.5 ml of MCB were placed in a thick-walled glass tube, which was sealed with a rubber liner and a metallic cap, see "Manipulation of Airsensitive Compounds" by D. F. Shriver, McGraw-Hill Book Company, New York, at pages 157°-158 (1969). The air was removed by slow sparging with nitrogen through a long needle reaching the bottom of the flask and escaping through another short syringe needle. The tube was placed in an oil bath which was heated at 135°-140° C. The sulfur was molten within a few minutes and the reaction mixture turned dark red. After 9 hours the tube was taken out of the oil bath and cooled to room temperature. The crystals of HMP, mp 178°-180° C., which formed were collected by filtration, washed with 2 ml MCB and dried in an oven at 70° C. The yield of HMP of 95.6% purity was 0.82 g (72.9%). HMP was identified by HPLC, NMR and GC/MS.

EXAMPLE 2

1.33 g (12 mmole) of DHP, sulfur (0.51 g, 16 mmole), and 6 ml MCB were placed in a thick-walled glass tube. This experiment was carried out as Example 1, but no N$_2$ was sparged during the reaction. The pressure of H$_2$S (25 psi) which developed was intermittently released through a needle valve. After 7.5 hours at 135°-140° C. the reaction mixture was cooled to room temperature, the precipitated off-white crystals of HMP were filtered off, washed with 2.0 ml MCB and dried in an oven at 70° C. to give 0.82 g (62.7%) of HMP, mp 178°-180° C. The HMP contained 0.4% by weight sulfur.

EXAMPLE 3

13.3 g (120 mmole) of DHP (90.1% purity), sulfur (4.16 g, 130 mmole), and 35 ml of Tenneco 500-100 were placed in a 100 ml 3-necked round bottom flask, equipped with a N$_2$ sparger, reflux condenser with an outlet to an aqueous NaOH scrubber and thermometer. The reactor was placed in an oilbath at 138°-142° C. After 6 hours the reaction mixture was cooled to room temperature. The crystalline HMP was filtered off and washed with 10 ml Tenneco 500-100 to give 8.75 g (74.5%) of HMP. Purity was 95.5% as determined by HPLC.

EXAMPLE 4

DHP of 90.1% purity 13.3 g (120 mmole), sulfur (4.16 g, 130 mmole) and 35 ml of MCB were introduced into a 100 ml 3-necked round bottom flask, equipped with N$_2$ sparger, reflux condenser with an outlet to an aqueous NaOH scrubber and thermometer. The reactor was placed in an oilbath heated to 138°-143° C. After 11 hours the reaction mixture was cooled to room temperature. The crystalline product was separated by filtration and washed with 10 ml MCB to give HMP of 96.4% purity as determined by HPLC. The yield of 8.1 g was 66.4%. The filtrate was extracted with 30 ml H$_2$O. The water extract was treated with 0.4 g of Darco ® activated carbon, filtered and evaporated to dryness to give an additional 2.6 g of material which contained 87.7% HMP. The total yield of HMP was 83.3%.

EXAMPLE 5

The solvent 1,2,4-trichlorobenzene (TCB) was removed by distillation (80° C. and 20 mm Hg pressure) from 45 g of a TCB solution containing 27% by weight DHP. The distillate of 29 g contained about 2% DHP, 20 ml of MCB as well as sulfur (3.5 g, 109.5 mmole) was added to the undistilled material in a 3-necked round bottom flask. The mixture was heated at 135°-138° C. for 7 hours with continuous sparging with nitrogen. After cooling to room temperature the mixture was poured with stirring into 20 ml of H$_2$O. After separating the layers the organic layer was extracted with 10 ml of H$_2$O. The combined water extracts were treated with 0.4 g of Darco ®, filtered and evaporated to dryness.

The crude HMP thus obtained was recrystallized from toluene/methanol to give 9 g (79%) of pure HMP.

EXAMPLE 6

60 g of a TCB solution containing 20.7% by weight DHP (112 mmole) were placed in a 100 ml 3-necked round bottom flask as in Example 4 together with sulfur (3.7 g, 115.6 mmole). The reaction mixture was kept at 135°–140° C. for 7 hours while continuously sparged with nitrogen, cooled to 80° C. and poured into 30 ml of H$_2$O with stirring. The layers were separated and the organic layer was extracted with 15 ml of water. The aqueous extracts were combined, treated with 0.2 g of Darco ®, filtered and the filtrate was evaporated to dryness yielding a light brown material, from which a total of 8.5 g (69.7%) HMP was obtained by recrystallization from a mixed solvent of methanol:ethyl acetate (1:4).

REFERENCE EXAMPLE 5

To 4.2 g of 5-methyl-2-pyridone was added 15 ml of POCl$_3$ at 25° to 34° followed by 3 g of PCl$_5$. The reaction mixture was stirred and heated at 110° C. for 4 hours and gradual solution took place. The product was added to 100 g of crushed ice and neutralized to pH 8 with 80 ml of 15% sodium hydroxide while cooling. The aqueous solution was extracted 5 times with 24 ml of methylene chloride each. The extracts were analyzed by GLC and evaporated at 40° C. at 4 mm of Hg to a constant weight. The yield was 3.9 g of 2-chloro-5-methylpyridine.

Elemental Analysis: Cl, 26.55% (Calculated, 27.8%): N, 10.75% (Calculated, 10.98%).

What is claimed is:

1. A method of producing 5-methyl-2-pyridone of the following formula (I):

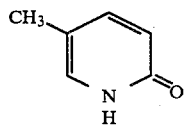

which comprises:

(a) dehydrogenating 5-methyl-3,4-dihydro-2(1H)-pyridone of the following formula (II):

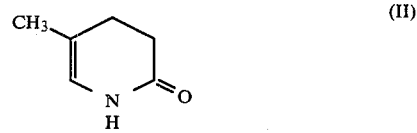

by reaction with sulphur at a temperature in the range of 130°–160° C. in the presence of an aromatic solvent wherein the molar ratio of sulphur/dihydropyridone of formula (II) is less than about 2:1; and (b) recovering the resulting 5-methyl-2-pyridone of formula (I) from the reaction mixture by either:
  (i) cooling the reaction mixture from the reaction temperature, allowing the pyridone of formula (I) to crystallize and filtering the reaction medium; or
  (ii) extracting the reaction mixture with water.

2. The method of claim 1, wherein said dehydrogenation is conducted at a temperature of about 130° to 140° C.

3. The method of claim 1, wherein said molar ratio is about 1:1 to less than 2:1.

4. The method of claim 1, wherein said molar ratio is slightly over 1:1 to about 1.3:1.

5. The method of claim 1, wherein said solvent does not contain oxygen.

6. The method of claim 1, wherein said solvent is an aromatic hydrocarbon or an aromatic halogenated hydrocarbon.

7. The method of claim 6, wherein said solvent is monochlorobenzene.

8. The method of claim 1, wherein hydrogen sulfide gas produced during said dehydrogenation is continuously removed.

9. The method of claim 8, wherein hydrogen sulfide gas produced during said dehydrogenation is continuously removed by passing an inert gas through the reaction mixture.

10. The method of claim 9, wherein said inert gas is nitrogen.

* * * * *